(12) United States Patent
Uihlein

(10) Patent No.: US 8,540,648 B2
(45) Date of Patent: Sep. 24, 2013

(54) GUIDE WIRE WITH MARKING PATTERN

(75) Inventor: Bernhard Uihlein, Dettingen (DE)

(73) Assignee: EPflex Feinwerktechnik GmbH, Dettingen/Erms (DE)

(*) Notice: Subject to any disclaimer, the term of this patent is extended or adjusted under 35 U.S.C. 154(b) by 440 days.

(21) Appl. No.: 12/921,513

(22) PCT Filed: Mar. 11, 2008

(86) PCT No.: PCT/EP2008/001925
§ 371 (c)(1),
(2), (4) Date: Sep. 8, 2010

(87) PCT Pub. No.: WO2009/112048
PCT Pub. Date: Sep. 17, 2009

(65) Prior Publication Data
US 2011/0021951 A1    Jan. 27, 2011

(51) Int. Cl.
*A61B 5/00* (2006.01)
(52) U.S. Cl.
USPC .......................................................... 600/585
(58) Field of Classification Search
USPC .......................................................... 600/585
See application file for complete search history.

(56) References Cited

U.S. PATENT DOCUMENTS

| | | | |
|---|---|---|---|
| 6,613,002 B1 | 9/2003 | Clark et al. | |
| 7,278,973 B2 * | 10/2007 | Iwami et al. | 600/585 |
| 7,833,175 B2 * | 11/2010 | Parins | 600/585 |
| 2006/0149165 A1 | 7/2006 | Kennedy, II et al. | |

FOREIGN PATENT DOCUMENTS

| | | |
|---|---|---|
| DE | 80 20 180 U1 | 7/1980 |
| DE | 198 23 414 A1 | 6/1999 |
| DE | 102 43 261 A1 | 3/2004 |
| DE | 102 55 030 A1 | 6/2004 |
| DE | 102 43 261 B4 | 3/2006 |
| EP | 0 714 315 B1 | 6/1996 |
| EP | 1 607 035 A1 | 12/2005 |

OTHER PUBLICATIONS

Form PCT/IB/338 (One (1) page); Form PCT/IB/373 (One (1) page); Form PCT/ISA/237 (Seven (7) pages).
International Search Report dated Jan. 13, 2009 with English translation (six (6) pages).

* cited by examiner

*Primary Examiner* — Max Hindenburg
(74) *Attorney, Agent, or Firm* — Crowell & Moring LLP

(57) ABSTRACT

A guide wire for a medical instrument, such as an endoscope, has a marking pattern, which extends at least across part of the axial length of the guide wire and includes markings of different marking types that can be sensed. On the guide wire, markings of first and second marking types are formed by marking surfaces, of which the marking surfaces of at least the first marking type each extend across only part of the circumferential surface of the guide wire and across only part of the axial length of the marking pattern, and in the axial direction of the guide wire follow each other at a distance by at least one interposed marking surface of the second marking type. At least one longitudinal marking strip is formed as a marking of a third marking type, which extends continuously across the axial length of the marking pattern.

15 Claims, 6 Drawing Sheets

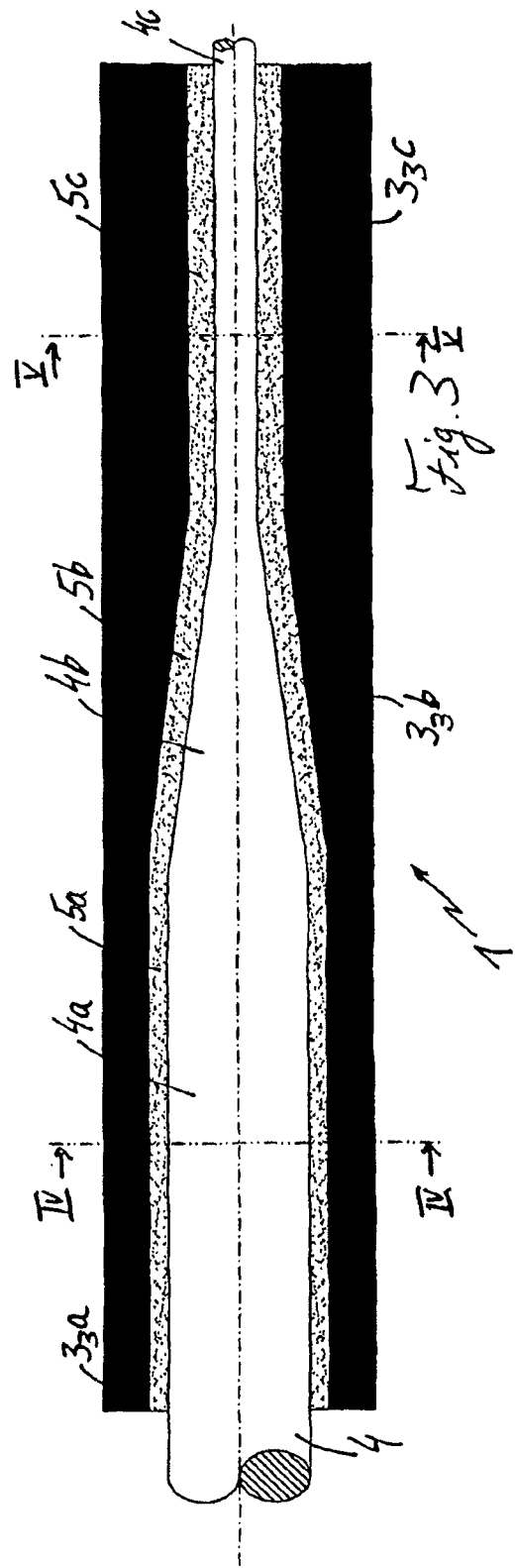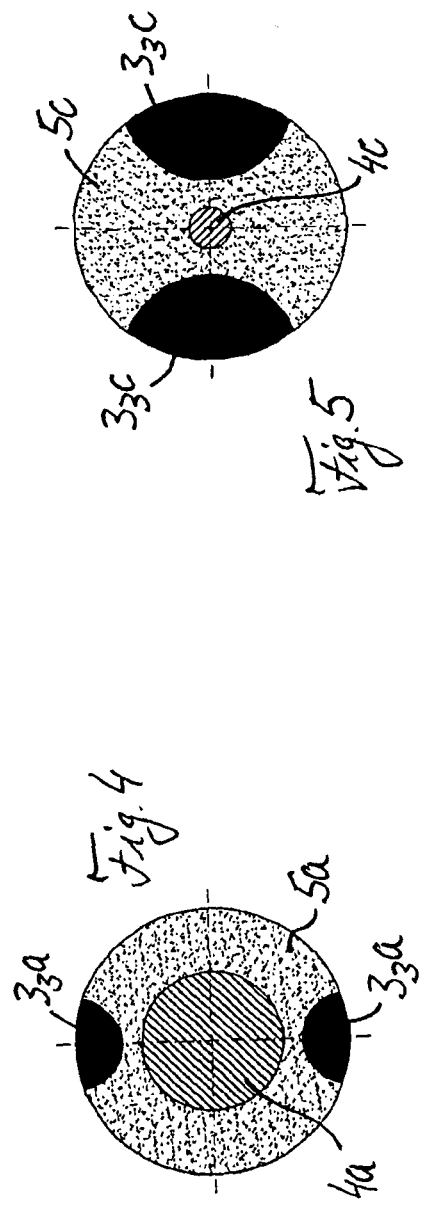

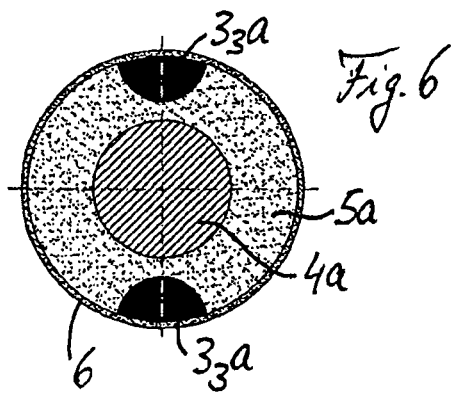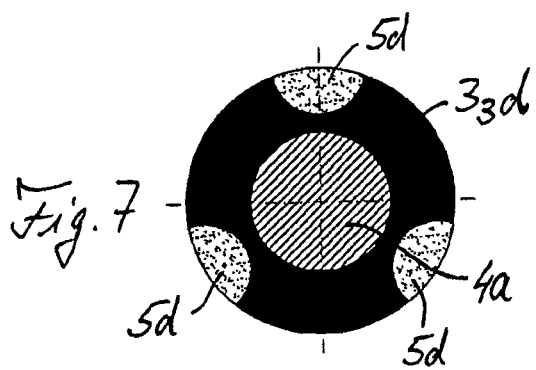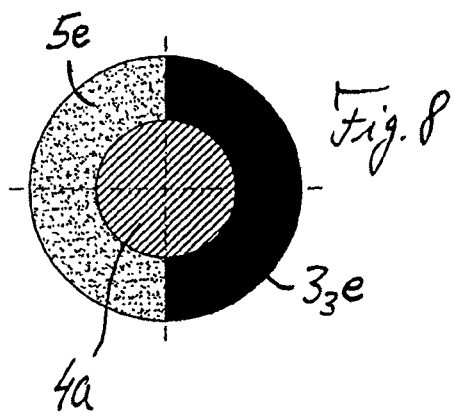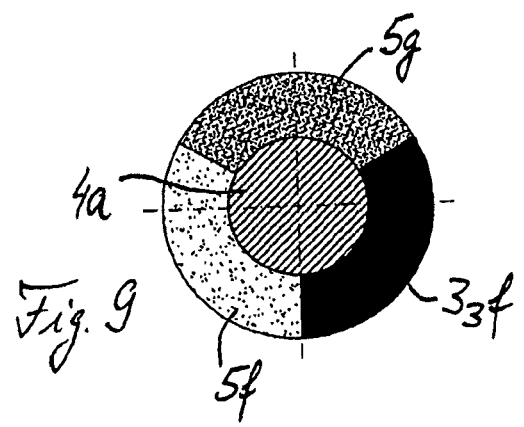

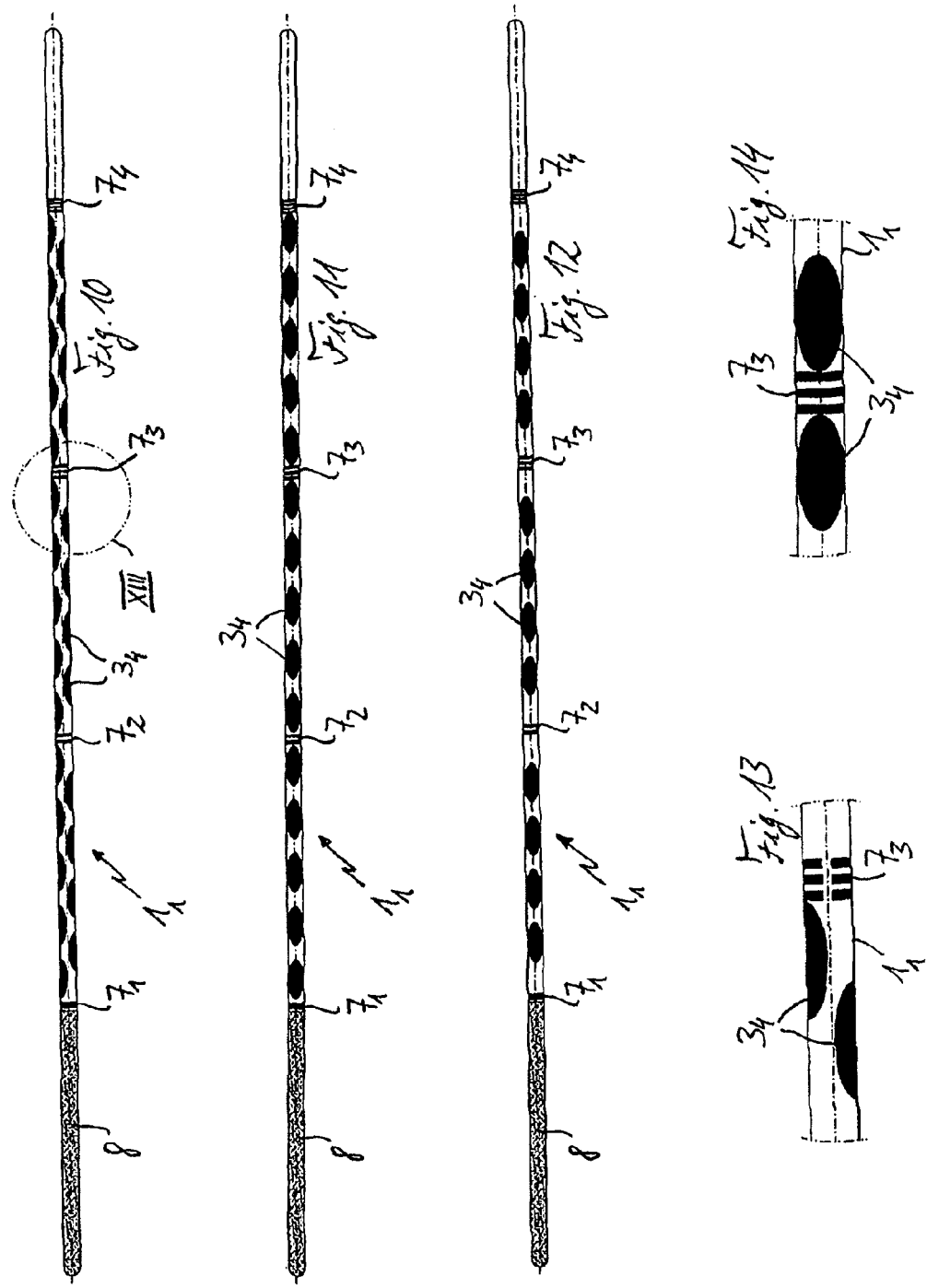

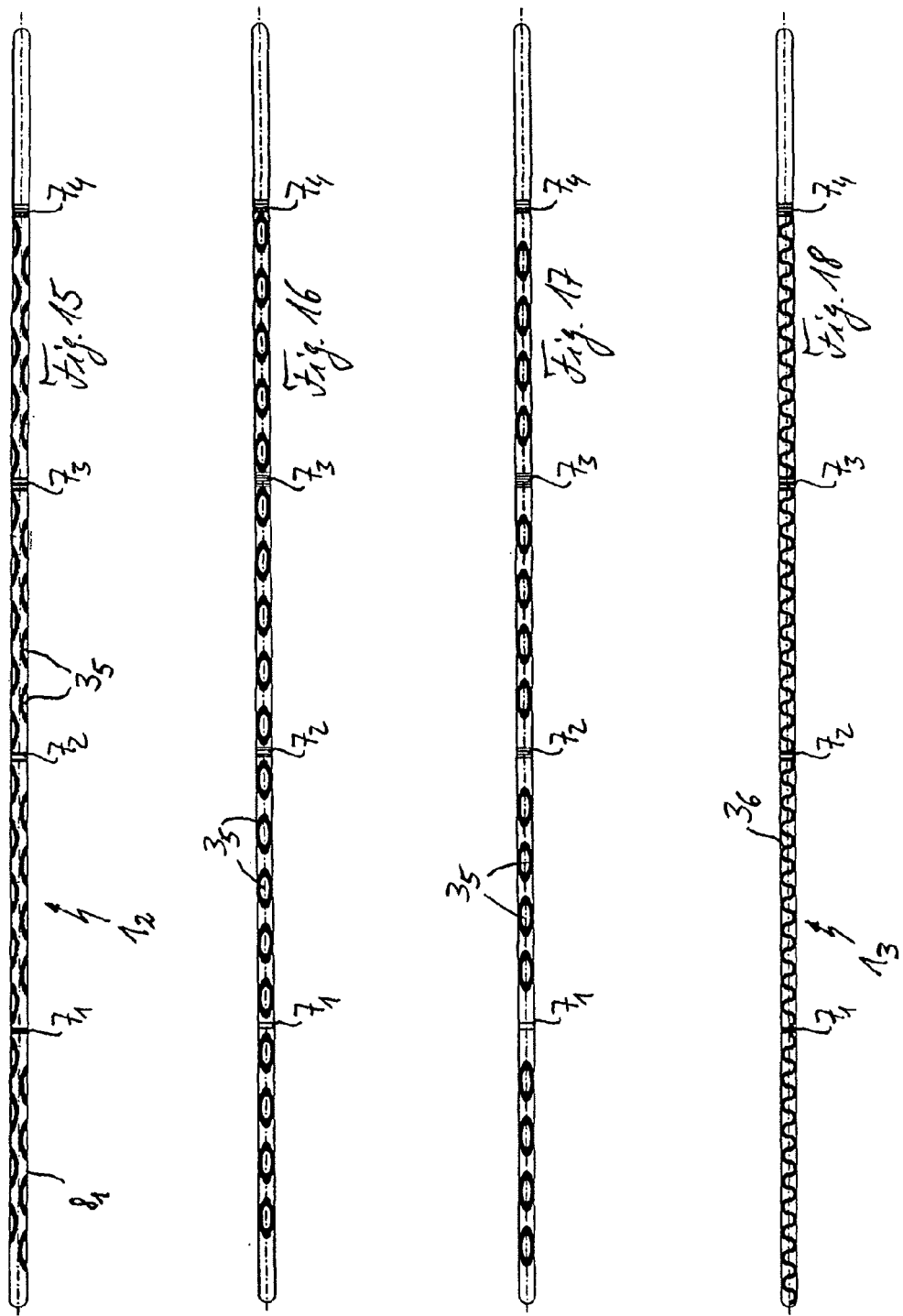

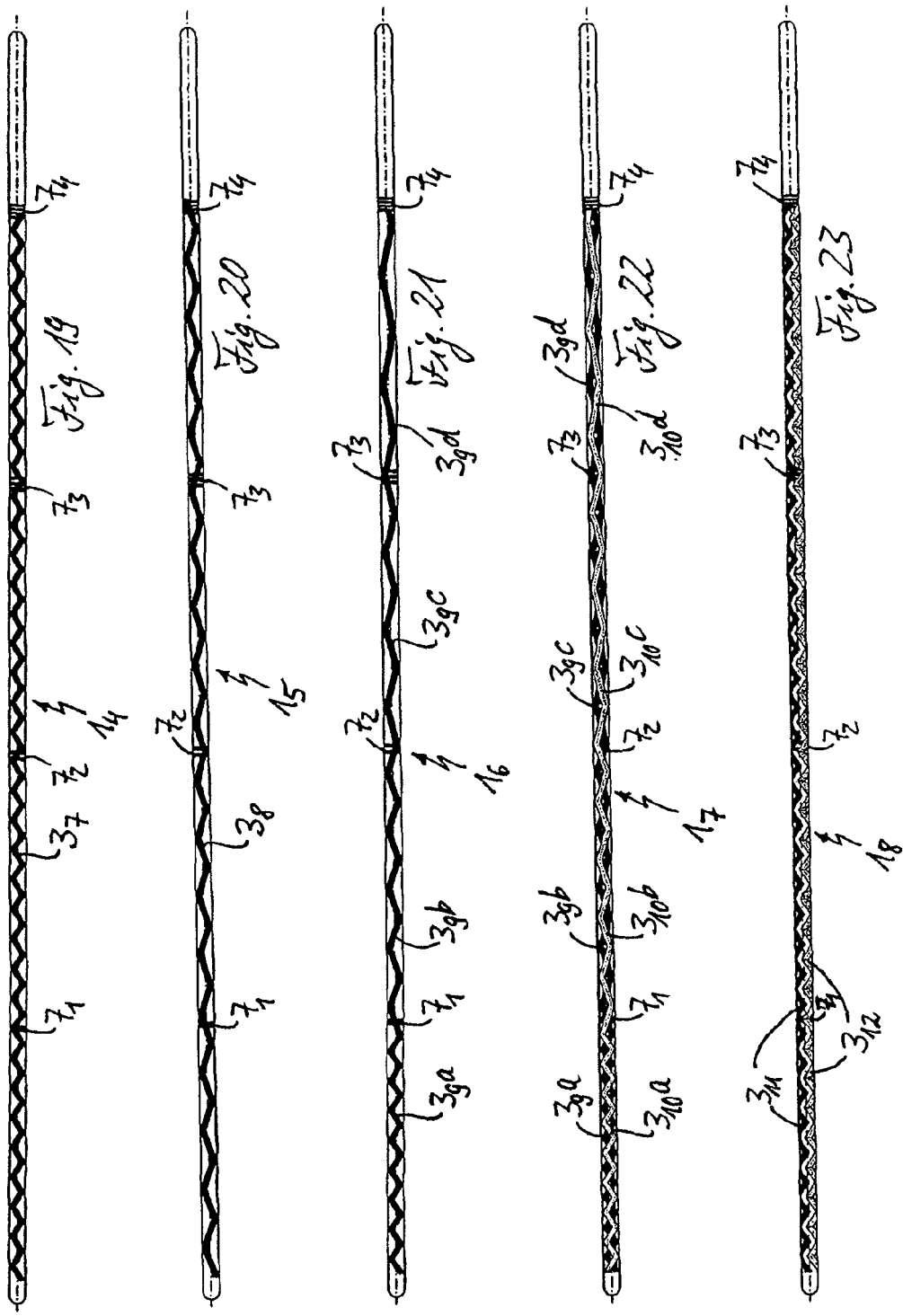

GUIDE WIRE WITH MARKING PATTERN

BACKGROUND AND SUMMARY OF THE INVENTION

The invention relates to a guide wire that is intended for a medical instrument and that exhibits a marking pattern which extends over at least a part of the axial length of the guide wire and comprises detectable markings of a plurality of different types of markings.

Guide wires of this type are used especially in surgical instruments, like endoscopes. The marking pattern serves to make it easier to detect the momentary position of the guide wire in use, to which end the markings can be detected, for example, by eye or by X-rays.

In addition, it is known to construct the marking pattern of at least two different marking rings that follow one after the other alternatingly in the longitudinal direction of the guide wire and extend over the entire circumferential length of the guide wire. This marking pattern makes it possible to perceive the axial motion and/or the feed motion of the guide wire from the sequence of marking rings that alternate—for example, varying in brightness—in the axial direction of the wire.

In order to detect, in addition to the axial motion, also a rotational motion of the guide wire by sensing the marking pattern, it is known to provide a marking pattern composed of at least two marking spirals that are arranged with alternating windings. This pattern can be achieved, for example, with a background color on the periphery of the guide wire and a helical strip of a contrasting color that is applied on said periphery, as disclosed in the patent specification EP 0 714 315 B1. The published patent application DE 198 23 414 A1 shows an alternative implementation, where a plurality of different helical spring members with alternating windings are inter-wound and provide their own marking externally, so that the result is altogether two or more different, detectable marking spirals.

The known marking patterns with marking spirals are not always easy to produce. In addition, there may be detection problems when the guide wire performs a combined axial and rotational motion that matches to a high degree the course of the marking spirals because then it is not very likely that the defined detection point will show the marking change-over that signals the motion.

The patent specification DE 102 43 261 B4 discloses a guide wire that makes it possible to detect the motion of the guide wire not only during pure axial or rotational motions but also during combined axial and rotational motions. In order to achieve this goal, the markings of the guide wire are configured in such a way that the markings of at least a first of many different marking types are formed by marking surfaces that extend only over a part of the circumferential length of the guide wire and only over a part of the axial length of the marking pattern and follow one after the other in the axial direction of the guide wire with an offset in the circumferential direction and/or with axial spacing.

Working on this basis, the published patent application DE 102 55 030 A1 proposes that the markings of at least two different marking types be configured as the marking surfaces that extend only over a part of the circumferential length of the guide wire and only over a part of the axial length of the marking pattern and follow one after the other in the axial direction of the guide wire with an offset in the circumferential direction and/or with axial spacing.

The invention is based on the technical problem of providing a guide wire of the type described above such that its marking pattern further facilitates the detection of the motion of the guide wire as compared to the aforementioned prior art.

The invention solves this problem by providing a guide wire that is intended for a medical instrument and that comprises a marking pattern, which extends over at least a part of the axial length of the guide wire and comprises detectable markings of at least three different types of markings. Markings of a first and second marking type are formed by the marking surfaces, of which the marking surfaces of at least the first marking type extend only over a part of the circumferential length of the guide wire and only over a part of the axial length of the marking pattern and follow one after the other in the axial direction of the guide wire with spacing by at least one intermediate marking surface of the second marking type. At least one longitudinal marking strip is formed as a marking of a third marking type, which extends continuously over the axial length of the marking pattern.

The invention also solves this problem by providing a guide wire that is intended for a medical instrument and that comprises a marking pattern, which extends over at least a part of the axial length of the guide wire and comprises detectable markings of at least two different types of markings. Markings of a first marking type are formed by transverse strip structures, which can be distinguished from each other and are arranged with axial spacing in relation to each other and extend over more than half the guide wire circumference in the circumferential direction. Markings of a second marking type are provided in the form of marking surfaces and/or longitudinal marking strips in at least the area between each pair of transverse strip structures, wherein the marking surfaces extend only over a part of the circumferential length of the guide wire and only over a part of the axial length of the marking pattern and follow one after the other in the axial direction of the guide wire with an offset in the circumferential direction and/or with axial spacing, or the longitudinal marking strips extend continuously between the transverse strip structures.

In one embodiment, the guide wire, according to the invention, has detectable markings of at least three different marking types, two of which are achieved by marking surfaces that are arranged in a special way that makes it possible to perceive the axial motions of the guide wire. In this case these marking surfaces can also contribute to the detection of the rotational position of the guide wire. With respect to the properties and the advantages of the marking surfaces of the first and the second marking type reference can also be made to the aforementioned documents DE 102 43 261 B4 and DE 102 55 030 A1, which describe the respective guide wires that exhibit such types of marking surfaces. In addition, the detection of the rotational position is facilitated in that at least one longitudinal marking strip is formed as a third marking type that extends continuously over the axial length of the marking pattern.

In a further development of the invention, the marking surfaces of the first and/or second marking type are formed by ring segment marking surfaces that are rectangular, diamond shaped or circular in the circumferential development of the guide wire, that is, by means of geometric pattern elements that are easy to detect and simple to produce. In this context the term "circular" comprises not only round surfaces, but also elliptical, oval and similar surfaces. In an additional embodiment, the marking surfaces of the first and the second marking type are formed by the respective ring segment marking surfaces that exhibit a definable expansion in the circumferential and axial direction of the guide wire and are arranged so as to alternate in the axial direction of the guide wire, a feature that makes it possible to detect the axial position of the guide wire in an advantageous way. Even the detection of the rotational position of the guide wire can be facilitated by the respective arrangement of the ring segment marking surfaces, for example, in that in an embodiment of the invention, the ring segment marking surfaces of the respective marking type are arranged with an offset in the circumferential direction.

The longitudinal marking strip(s) can extend, without or with the circumferential direction component—that is, in exactly the axial direction or as an alternative at an oblique angle thereto and/or in the form of a helical line with a more or less large circumferential direction component.

In a further development of the invention, a plurality of longitudinal marking strips are arranged so as to be spaced apart in the circumferential direction, and the marking surfaces of the first and the second marking type are located between the longitudinal marking strips. Such a marking pattern facilitates even more the detection of the axial and rotational position of the guide wire.

In a further development of the invention, the markings of the first, second and/or third marking type can be detected by eye or by X-rays. In particular, it can be provided that one of the marking types can be detected visually, and another marking type can be detected by X-rays, for example, by providing visually detectable marking surfaces and one or more radiographically detectable longitudinal marking strips.

In a further development of the invention, the longitudinal marking strip(s) is (are) integrated into a sheathing of a core wire of the guide wire by using a suitably detectable material for the sheathing in a peripheral area forming the longitudinal marking strip(s). In this case the material is different from the material(s) for the remaining area of the sheathing. This feature allows the longitudinal marking strip(s) to be produced in an advantageous way even from a manufacturing viewpoint, for example, when they are provided as radiographically detectable longitudinal strips.

In an additional embodiment of this technique, the sheathing in a distal end section of the guide wire is formed with a larger cross sectional area than in an adjoining section, as a result of which a tapering of the core wire in this distal end section is compensated at least partially with respect to the outside diameter of the guide wire. Then the at least one longitudinal marking strip exhibits in the distal end section a larger cross sectional area than in its adjoining guide wire section, a feature that can be used, for example, for an improved radiographic visibility of the distal end section of the guide wire.

In the case of the guide wire according to another embodiment, markings of a first marking type in the form of transverse strip structures are combined with markings of a second marking type in the form of marking surfaces or longitudinal marking strips in the area between each pair of transverse strip structures.

In this case the marking surfaces extend only over a part of the circumferential surface of the guide wire and only over a part of the axial length of the marking pattern and follow one after the other in the axial direction of the guide wire with an offset in the circumferential direction and/or with axial spacing, or the longitudinal marking strips extend continuously between the transverse strip structures. The transverse strip structures can be distinguished from each other and arranged so as to be axially spaced apart from each other and extend over more than half of the guide wire periphery in the circumferential direction. Even this marking pattern is capable of improving in an advantageous way the detection of the axial and rotational position of the guide wire. With respect to these properties and advantages of the marking surfaces reference can be made in turn to the aforementioned publications DE 102 43 261 B4 and DE 102 55 030 A1. The additional transverse strip structures facilitate to a high degree the detection of the axial position of the guide wire.

In a further development of the invention, the differentiable transverse strip structures are formed in an advantageous way in terms of production engineering by use of a varying number of closely adjacent individual strips.

In a further development of the invention, the marking surfaces are formed by ring segment marking surfaces that are rectangular, diamond shaped, oval or circular in the circumferential development of the guide wire, where with respect to their properties and advantages reference is made to the above description. In this respect the marking surfaces can be configured so as to cover the whole surface area or the grooved area.

In a further development of the invention, a plurality of longitudinal marking strips are arranged so as to be offset in the area between each pair of transverse strip structures in the circumferential direction, thus improving even more the detection of the rotational position of the guide wire.

In a further development of the invention, at least one of the longitudinal marking strips has the shape of a wavy line or zigzag, as a result of which the longitudinal marking strip also supports the detection of the axial position of the guide wire. In an additional embodiment of this technique at least two longitudinal marking strips exhibit different wavy lines or zigzags in the different axial areas between the respective transverse strip structures, a feature that additionally facilitates the detection of the axial position of the guide wire.

Advantageous embodiments of the invention are shown in the drawings and are described below.

BRIEF DESCRIPTION OF THE DRAWINGS

FIG. 3 is a longitudinal sectional view showing a piece of a front area of a guide wire of the type depicted in FIG. 1 or 2;

FIG. 4 is a cross sectional view along a line IV-TV of FIG. 3;

FIG. 5 is a cross sectional view along a line V-V of FIG. 3;

FIG. 6 is a cross sectional view that corresponds to FIG. 4 and shows a variant with an additional outer layer;

FIG. 7 is a cross sectional view that corresponds to FIG. 4 and shows a variant with a core wire sheathing forming three longitudinal marking strips;

FIG. 8 is a cross sectional view that shows a variant with a core wire sheathing constructed of two different material halves;

FIG. 9 is a cross sectional view that corresponds to FIG. 8 and shows a variant with a core wire sheathing constructed of three different material segments;

FIG. 10 is a side view of a guide wire with a marking pattern composed of axially spaced, distinguishable transverse strip structures and marking surfaces that cover the entire surface area following a distal end section of a guide wire;

FIG. 11 is a top view showing the guide wire of FIG. 10 from the top;

FIG. 12 is a top view showing the guide wire of FIG. 10 from the bottom;

FIG. 13 is a view showing a piece of an area XIII from FIG. 10 for a variant of the transverse strip structures;

FIG. 14 is a top view showing the cutout area of FIG. 13 from the top;

FIG. 15 is a view of a guide wire that corresponds to FIG. 10 for a variant with a marking pattern and grooved marking surfaces that also extend in the distal end area;

FIG. 16 is a top view showing the guide wire of FIG. 15 from the top;

FIG. 17 is a top view showing the guide wire of FIG. 15 from the bottom;

FIG. 18 is a view of a guide wire that corresponds to FIG. 15 for a variant with longitudinal marking strips in the form of wavy lines, instead of marking surfaces;

FIG. 19 is a view of a guide wire that corresponds to FIG. 18 for a variant with zigzagging, instead of wavy, longitudinal marking strips;

FIG. 20 is a view of a guide wire that corresponds to FIG. 19 for a variant at a flatter zigzag angle of the zigzagging longitudinal marking strips;

FIG. 21 is a view of a guide wire that corresponds to FIG. 19 for a variant with zigzagging longitudinal marking strips at a different zigzag angle in the different areas between the transverse strip structures;

FIG. 22 is a view of a guide wire that corresponds to FIG. 21 for a variant with axially offset zigzag longitudinal marking strips; and FIG. 23 is a view of a guide wire that corresponds to FIG. 21 for a variant with zigzag longitudinal marking strips that are offset axially and in the circumferential direction.

DETAILED DESCRIPTION OF THE DRAWINGS

Figure 1:
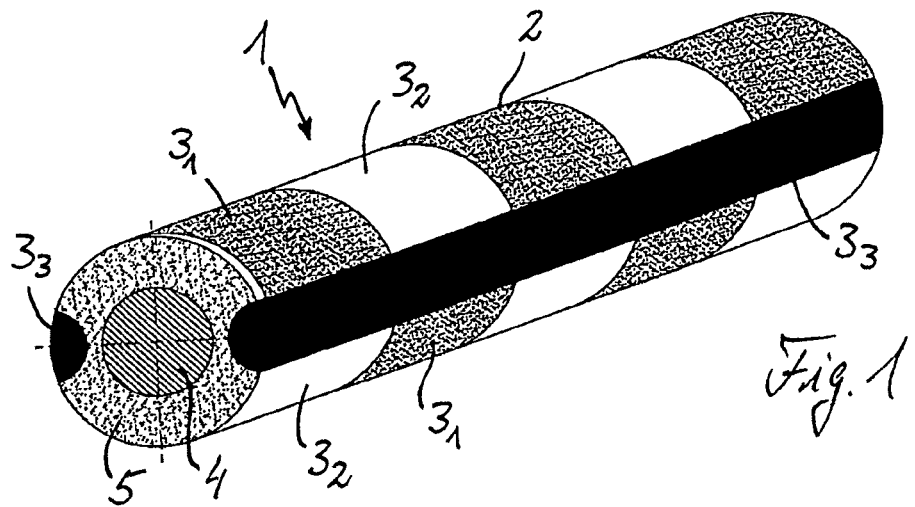
FIG. 1 is a schematic perspective view showing a piece of a guide wire with a marking pattern that includes semi-circular marking surfaces and longitudinal marking strips that are offset axially and in the circumferential direction.

A guide wire 1, of which a representative section is shown as a schematic drawing in FIG. 1, has at least one marking pattern 2 in the illustrated area.

This marking pattern 2 includes semi-circular first marking surfaces $3_1$, which are depicted as gray surface areas in FIG. 1, and semi-circular second marking surfaces $3_2$, which are depicted as white surface areas in FIG. 1, as well as two longitudinal marking strips $3_3$. The two longitudinal marking strips $3_3$ are offset by 180 deg. in the circumferential direction and extend linearly in the axial direction of the guide wire 1 continuously over the entire length of the marking pattern 2. The first and second marking surfaces $3_1$, $3_2$ extend in the circumferential direction between the two longitudinal marking strips $3_3$ with a predetermined axial length. In this case they are arranged alternatingly in the axial direction of the guide wire 1. In addition, the first marking surfaces $3_1$, which follow one after the other in the axial direction, and the second marking surfaces $3_2$, which also follow one after the other in the axial direction, are arranged so as to be offset by 180 deg. in the circumferential direction and so as to be offset by their axial length in the axial direction. That is, opposite a first marking surface $3_1$ on, for example, the upper side of the guide wire 1 in FIG. 1 lies a second marking surface $3_2$ on the other side—the bottom side of the guide wire 1 in FIG. 1.

The three marking types, that is, the first and second marking surfaces $3_1$, $3_2$ and the longitudinal marking strips $3_3$, are different in at least one sensing parameter, that is, in at least one physical parameter, which is sensed for detection of the motion, particularly for detection of the axial position and the rotational position of the guide wire 1. This physical parameter can be sensed, for example, visually, in that the three marking types are of different colors and/or brightness for example. In addition or as an alternative to the visual detectability, a radiographic visibility for at least one of the three marking types, for example, the marking strips $3_3$, may be provided. Suitable materials for the different, visually and/or radiographically detectable marking types are well known to the person skilled in the art and, hence, do not require any further explanation at this point.

The described structure of the marking pattern 2 allows a reliable detection of both pure axial motions as well as also pure rotational motions and combined axial and rotational motions of the guide wire 1. In this respect the axial motion or rather the axial position of the guide wire 1 can be detected by the sequence of first and second marking surfaces $3_1$, $3_2$ alternating in the axial direction, and the rotational motion or rather the rotational position of the guide wire 1 can be detected by means of the rotational position of the longitudinal marking strips $3_3$ and the first and second marking surfaces $3_1$, $3_2$ that are arranged so as to be offset on the two opposite peripheral halves of the guide wire 1.

As FIG. 1 also shows, the guide wire 1 contains a core wire 4, which is made of a material that is customary for this purpose, for example, a stainless steel or nitinol material, which is enveloped by a protective sheathing 5. In this case the sheathing 5 serves as a carrier of the marking pattern 2. In the illustrated example 1 the first and second marking surfaces $3_1$, $3_2$ form the outer peripheral areas of the sheathing 5, where the shape of these outer peripheral areas is configured differently so as to match. Moreover, the two longitudinal marking strips $3_3$ are integrated in the sheathing 5 as the webs having an approximately semi-circular cross section. At the same time the longitudinal marking strips $3_3$ can be applied on the core wire 4 together with the remaining sheathing material by means of conventional extrusion methods. In the illustrated guide wire section from FIG. 1, the longitudinal marking strips $3_3$ extend into the remaining sheathing material in the radial direction as far as somewhat more than half the thickness of the sheathing 5. It is self-evident that the material of the longitudinal marking strip $3_3$ differs in a suitable way from the remaining sheathing material, for example, in that it is configured as radiographically visible, whereas the rest of the sheathing material is made of a non-radiographically visible material. Furthermore, it is clear that the remaining sheathing material is chosen, as a function of the requirement and application, so as to be, for example, visually detectable in such a way that it forms simultaneously the material for the first or the second marking surfaces $3_1$, $3_2$, so that in order to form the two marking surface types $3_1$, $3_2$, only the marking surfaces of the one type has to be applied additionally on the outside of the sheathing 5 in the corresponding areas. The uncoated axial intermediate areas of the sheathing material form the marking surfaces of the other marking type without the additional coating effort.

Figure 2:
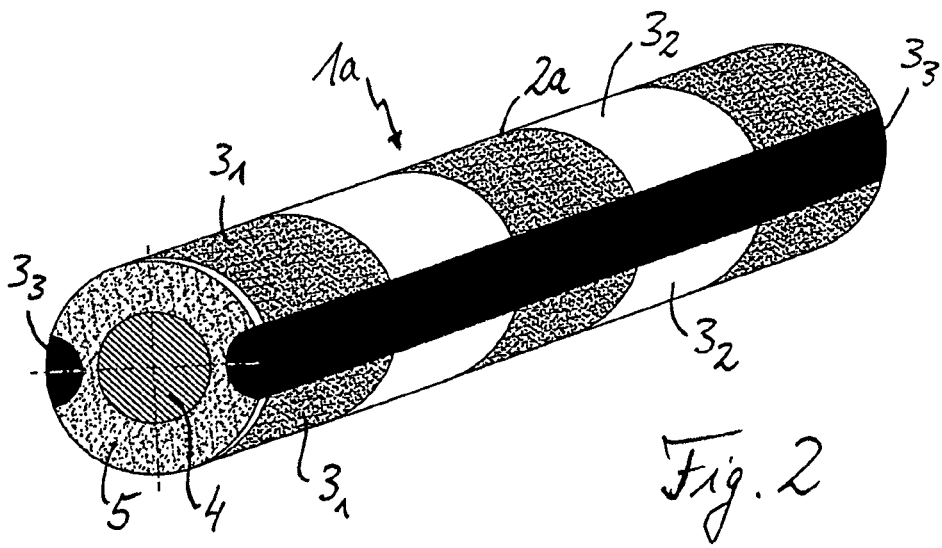
FIG. 2 is a view that corresponds to FIG. 1 and shows a variant with semi-circular marking surfaces arranged without an offset in the circumferential direction.

FIG. 2 shows a variant of the guide wire 1a with a modified marking pattern 2a, which matches the pattern from FIG. 1 with the exception that the first marking surfaces $3_1$ are opposite each other on the two peripheral halves of the guide wire 1a without an axial offset. Moreover, the same holds true for the second marking surfaces $3_2$. Furthermore, the same reference numerals for identical or functionally equivalent elements are used here and below for the various embodiments for the sake of a better overview, so that in this respect reference can be made to the above descriptions of the embodiment from FIG. 1. Despite the arrangement of each of the two marking surface types without the axial offset on the two peripheral halves, the marking pattern 2a from FIG. 2 makes it possible to detect the rotational position of the guide wire 1a owing to the longitudinal marking strips $3_3$. Depending on the production method, the marking pattern 2a from FIG. 2 can be achieved at a comparatively low cost of production.

FIG. 3 is a view of the guide wire 1 from FIG. 1 cut longitudinally through the longitudinal plane of symmetry from FIG. 1. In this case a piece of the guide wire 1 is depicted in a section, where the core wire 4 tapers off, and in a distal section that follows on the right in FIG. 3, and in a section that follows on the left in FIG. 3. Owing to the tapering of the core wire 4 from its thicker part 4a in the shaft section to a thinner distal part 4c over a conically tapering section 4b, the guide wire 1 is more flexible in the distal end area. Since the thickness of the sheathing expands in a counterclockwise manner from its shaft section 5a over its transition section 5b to its distal section 5c, the outside diameter of the guide wire 1 from the shaft section to the distal end area stays constant. At the same time the cross sectional area of the two longitudinal marking strips also increases correspondingly from their shaft section $3_3a$ over their transition section $3_3b$ to their distal end section $3_3c$, as illustrated by the cross sectional views in FIGS. 4 and 5, which show the guide wire in the shaft section and/or in the distal end section. This feature can be used, as needed, to enhance in a desired way the visibility of the distal end area of the guide wire 1, in that, for example, radiographic material is used for the longitudinal marking strips, and then the distal end area $3_3c$ of the longitudinal marking strips has proportionally more radiographically visible material than in its shaft section $3_3a$. The marking surfaces $3_1$, $3_2$ can be provided, when required, in both the distal section and in the shaft section of the guide wire 1 or in both sections in a way that is not shown in detail. Furthermore, it is obvious that in alternative embodiments the marking pattern 2, exhibiting the longitudinal marking strips $3_3$, can be provided in the shaft section and in the distal section or only in one of these two guide wire sections.

When required, the guide wire, according to FIG. 1 or FIG. 2, is provided with an additional outer skin 6, as shown in FIG. 6. In this case the outer skin 6 is provided, as a function of the requirement, over the entire axial length of the guide wire or only sectionally.

The outer skin 6 makes it possible to achieve a desired surface effect for the guide wire, for example, to improve its slip properties. The marking surfaces of the marking pattern can be integrated into the outer skin 6 or be configured thereon, as a function of the application. As an additional alternative it is possible for the outer skin 6 to envelop the marking surfaces $3_1$, $3_2$ as well as the longitudinal marking strips $3_3$, provided that their detectability is not impaired, a feature that in the case of visually detectable markings can be guaranteed, for example, by an optically transparent outer skin 6.

It is clear that it is possible for the two longitudinal marking strips that are used in the embodiments from FIGS. 1 and 2 to have a large number of variants for implementing the longitudinal strips for the marking pattern. To this end FIGS. 7 to 9 show some exemplary examples that are advantageous from a production viewpoint, because they can be manufactured, for example, by injection molding and/or extrusion techniques.

In the guide wire variant shown in FIG. 7, the sheathing is made, as in the above described embodiments, of two different materials. In this respect a first material forms a continuous base jacket about the core wire 4, depicted in a shaft section 4a in FIG. 7. Embedded into the periphery of this jacket with equidistant circumferential spacing 3 are the longitudinal web areas 5d of a second material that is different from the base material. Depending on the system design, the base material is, for example, a material that can be detected, for example, by X-rays or by eye and that is divided externally into three spaced longitudinal marking strips $3_3d$ by means of the three longitudinal webs 5d.

As an alternative the three longitudinal web areas 5d can act as the longitudinal marking strips. Then they are configured so as to be suitably detectable and different from the material of the base jacket.

Even in the guide wire variant shown in FIG. 8, the sheathing is made of two different materials. In this case the two materials form half of a ring of the sheathing of the core wire 4a. In this way this jacketing has two longitudinal strip areas that extend over 180 deg. and of which at least one acts as the detectable longitudinal marking strip $3_3e$. Thus, it is possible to provide, for example, a radiographically visible material for these longitudinal marking strips $3_3e$, whereas the other half of the ring 5e of the jacket is made of a non-radiographically visible material.

In the guide wire variant shown in FIG. 9, the jacketing is constructed of three ring segments that extend through 120 deg. and for which different materials are used in each case. Thus, one of the three ring segments forms a longitudinal marking strip $3_3f$, which can be detected, for example, by eye or by X-rays and which differs correspondingly from the two other ring segments 5f, 5g. These two remaining ring segments 5f, 5g in turn can be configured for fulfilling other marking purposes or other functional purposes. Thus, all three ring segments 5f, 5g, $3_3f$ can differ in their visually detectable coloration and/or in other physical properties or utilization.

It is self-evident that even the guide wire variants in FIGS. 7 to 9 provide in a manner that is not illustrated in detail the marking surfaces $3_1$, $3_2$, in addition to the longitudinal marking strip(s), for the purpose of forming the marking pattern 2. In this case the marking surfaces can be constructed, in particular, as corresponding surface areas on the outside of the peripheral part of the sheathing that does not act as the longitudinal marking strip, for example, only in the longitudinal web areas 5d of FIG. 7, when the base jacketing forms the longitudinal marking strips $3_3d$, or vice versa only in the area of the base jacketing, when the longitudinal web areas 5d form the longitudinal marking strips. Similarly the two marking surface types $3_1$, $3_2$ in the guide wire variant of FIG. 8 can be designed, for example, only on one of the two halves of the sheathing ring 5e, $3_3e$ and/or in the guide wire variant of FIG. 9 only on one or two of the three sheathing ring segments.

In all of the above described embodiments of the invention, the combination of two marking surface types $3_1$, $3_2$ with the longitudinal marking strip type $3_3$ enables the guide wire to be detected very advantageously in the axial and rotational position. It is clear that the related advantages also exist in other embodiments of the invention that are not shown. In this case the longitudinal marking strip(s) may not run exactly axially, but rather with an additional circumferential direction component along the length of the marking pattern. Then the respective longitudinal marking strip can extend, when required, from one to the other axial end of the marking pattern only over a predetermined fraction of the entire circumference of 360 deg. or can also extend helically over more than 360 deg.

In FIGS. 10 to 23 the guide wire is implemented with a marking pattern that combines the marking surfaces or longitudinal marking strips with the marking transverse strip structures in such a way that the result is an advantageous detection of the axial and rotational position of the guide wire. The common feature that all of the embodiments shown in the figures share is that they exhibit, as a first marking type, a plurality of distinguishable transverse strip structures that are arranged so as to be distributed over the marking pattern with axial spacing. The illustrated example implements the transverse strip structures by means of a varying number of individual transverse strips, in particular, a first transverse strip structure $7_1$ composed of a single transverse strip, a second transverse strip structure $7_2$ composed of two closely adjacent individual transverse strips, a third transverse strip structure $7_3$ composed of three closely adjacent individual transverse strips, and a fourth transverse strip structure $7_4$ composed of four closely adjacent individual transverse strips.

In addition, the marking pattern in a guide wire $1_1$ that is shown in FIGS. 10 to 12 contains markings of a second marking type in the form of oval marking surfaces $3_4$ that cover the whole surface and that are arranged in two axial rows in the areas between the transverse strip structures. In this respect they extend by approximately 180 deg. in the circumferential direction. In the case of the guide wire $1_1$ in FIGS. 10 to 12 the marking pattern is formed in a guide wire section adjacent to a distal end section, where the distal end section 8 is made of a flexible synthetic plastic material.

FIGS. 13 and 14 are enlarged views of a piece of the guide wire $1_1$ from FIGS. 10 to 12 in the area of the third transverse strip structure $7_3$ that is formed by three individual transverse strips. In this case the figures illustrate a variant, where, as an alternative to a closed embodiment that is shaped like a ring, the individual transverse strips are implemented as open rings that extend over a circumferential angle of somewhat less than 360 deg.

A guide wire $1_2$, shown in FIGS. 15 to 17, corresponds to that in FIGS. 10 to 12 with the modification that the marking pattern also extends in a distal end section $8_1$, and grooved ovals $3_5$ are provided as the marking surfaces. The distal end section $8_1$ can be formed, for example as explained in conjunction with FIG. 3, by means of a tapering core wire that is enveloped by a sheathing bearing the marking pattern in such a manner that a constant outside diameter of the guide wire $1_2$ in the distal end section $8_1$ and in the adjoining shaft section is maintained.

A guide wire $1_3$, shown in FIG. 18, differs from the guide wire in FIGS. 15 and 17 in that, instead of marking surfaces, wavy longitudinal marking strips $3_6$ are provided in the distal end section and between the transverse strip structures $7_1$ to $7_4$.

A similar guide wire $1_4$ is shown in FIG. 19, where, instead of wavy longitudinal marking strips, zigzagging longitudinal marking strips $3_7$ are provided. A guide wire $1_5$, shown in FIG. 20, corresponds to the guide wire from FIG. 19, where the only difference is that there are modified longitudinal marking strips $3_8$ with a larger zigzagging angle.

Whereas in the embodiments from FIGS. 19 and 20, identical longitudinal marking strips $3_7$, $3_8$ are configured in all of the areas between the transverse strip structures $7_1$ to $7_4$, FIG. 21 shows a guide wire $1_6$, where the major distinction between the zigzagging longitudinal marking strips $3_9 a$ to $3_9 d$ is their zigzag angle. This feature contributes to an even better detection of the axial position of this guide wire $1_6$.

FIG. 22 shows a guide wire $1_7$, in which, starting from the guide wire $1_6$ in FIG. 21, there are additional zigzagging longitudinal marking strips $3_{10}a$ to $3_{10}d$, which correspond in their zigzagging shape and their zigzag angle to the other respective longitudinal marking strips in the same guide wire section and are axially offset in relation to them only by half a pitch.

In this respect both zigzagging longitudinal marking strips are designed so as to be distinguishable from each other in the respective guide wire section, for example, by means of different coloration that can be detected by eye. Thus, the detection of the axial and rotational position of this guide wire $1_7$ can be improved even more.

FIG. 23 shows a guide wire $1_8$, where the marking pattern comprises not only the transverse strip structures $7_1$ to $7_4$ but also two zigzagging longitudinal marking strips $3_{11}$, $3_{12}$ in the distal end section and in the areas between the transverse strip structures, which are arranged so as to be offset by half the circumferential length of the guide wire $1_8$ and extend in the circumferential direction over about half the circumferential length. This marking pattern is also capable in an advantageous way of a reliable detection of the axial and rotational position of the guide wire $1_8$.

It is self-evident that other embodiments of the invention can be implemented by providing marking patterns that were not shown and that are the result of combinations of the marking pattern elements described with respect to the above embodiments. Thus, for example, there may be marking patterns that exhibit both one or more continuous longitudinal marking strips and alternating marking surfaces of the type shown in FIGS. 1 and 2 as well as transverse strip structures, as described with respect to the examples shown in FIGS. 10 to 23. Moreover, it is clear that there may be combined marking patterns, where a first guide wire section has one of the illustrated and above described marking patterns and an adjoining guide wire section or an additional guide wire section that is set apart from the former has a marking pattern that differs from the ones that were illustrated and described above.

The invention claimed is:

1. A guide wire for a medical instrument, comprising:
    a marking pattern, which extends over at least a part of the axial length of the guide wire and comprises detectable markings of at least three different types of markings;
    wherein markings of a first and second marking type are formed by marking surfaces, of which the marking surfaces of at least the first marking type each extend only over a part of the circumferential length of the guide wire and only over a part of the axial length of the marking pattern and follow one after the other in the axial direction of the guide wire with spacing by way of at least one intermediate marking surface of the second marking type; and
    wherein at least one longitudinal marking strip is formed as a marking of a third marking type, which extends continuously over the entire axial length of the marking pattern.

2. The guide wire according to claim 1, wherein the markings of at least one of the first marking type and the second marking type are formed by ring segment marking surfaces that are rectangular, diamond shaped or circular in a circumferential development of the guide wire.

3. The guide wire according to claim 2, wherein the markings of the first and the second marking type are formed by the respective ring segment marking surfaces that exhibit a definable expansion in the circumferential and axial direction of the guide wire and that are arranged so as to alternate in the axial direction.

4. The guide wire according to claim 3, wherein axially successive ring segment marking surfaces of each of the first and the second marking type form pairs, each pair being arranged with an offset in the circumferential direction.

5. The guide wire according to claim 1, wherein the at least one longitudinal marking strip extends with or without a circumferential direction component.

6. The guide wire according to claim 1, further comprising as the markings of the third marking type, a plurality of longitudinal marking strips, which are spaced apart in the circumferential direction, wherein the marking surfaces of the first and the second marking type are located in an area between the plurality of longitudinal marking strips.

7. The guide wire according to claim 1, wherein the markings of at least one of the first, second and third marking type are visually detectable or radiographically detectable markings.

8. The guide wire according to claim 1, further comprising:
a core wire; and
a sheathing, the sheathing enveloping the core wire;
wherein the at least one longitudinal marking strip is formed by the sheathing through the use of different materials for the sheathing.

9. The guide wire according to claim 8, wherein the core wire is tapered in a first distal end section of the guide wire as compared to an adjoining second section, and the sheathing in the distal end section has a larger cross sectional area than in the first section, wherein at least one longitudinal marking strip exhibits in the distal end section a larger cross sectional area than in the first section.

10. A guide wire for a medical instrument, comprising:
a marking pattern, which extends over at least a part of the axial length of the guide wire and comprises detectable markings of at least two different types of markings;
wherein markings of a first marking type are transverse strip structures, which are distinguishable from each other and are arranged with axial spacing in relation to each other and extend over more than half the guide wire circumference in the circumferential direction; and
wherein markings of a second marking type are at least one of marking surfaces and longitudinal marking strips in at least the area between each pair of transverse strip structures, wherein one of (a) the marking surfaces extend only over a part of the circumferential length of the guide wire and only over a part of the axial length of the marking pattern and follow one after the other in the axial direction of the guide wire with at least one of an offset in the circumferential direction and an axial spacing, and (b) the longitudinal marking strips extend continuously between the transverse strip structures.

11. The guide wire according to claim 10, wherein the differentiable transverse strip structures are formed by a varying number of closely adjacent individual strips.

12. The guide wire according to claim 10, wherein the marking surfaces of the second marking type are ring segment marking surfaces that are rectangular, diamond shaped, oval or circular in the circumferential development of the guide wire and that are of solid or hollow surface area shape.

13. The guide wire according to claim 10, wherein a plurality of longitudinal marking strips are arranged offset in at least one of the axial direction and the circumferential direction of the guide wire.

14. The guide wire according to claim 10, wherein at least one of the longitudinal marking strips has the shape of a wavy line or zigzag.

15. The guide wire according to claim 14, wherein at least two longitudinal marking strips, which are arranged in different axial areas between the respective transverse strip structures, exhibit different wavy line or zigzag forms.

* * * * *